(12) United States Patent
Pollock et al.

(10) Patent No.: US 7,604,775 B2
(45) Date of Patent: Oct. 20, 2009

(54) FLUID COLLECTING AND MONITORING DEVICE

(75) Inventors: Neil Pollock, Royston (GB); Richard Wilhelm Janse Van Rensburg, Longstanton (GB)

(73) Assignee: Bayer Healthcare LLC, Tarrytown, NY (US)

( * ) Notice: Subject to any disclaimer, the term of this patent is extended or adjusted under 35 U.S.C. 154(b) by 685 days.

(21) Appl. No.: 10/216,597

(22) Filed: Aug. 12, 2002

(65) Prior Publication Data

US 2004/0028558 A1  Feb. 12, 2004

(51) Int. Cl.
*G01N 21/00* (2006.01)
*B01L 3/02* (2006.01)
*G01N 1/10* (2006.01)

(52) U.S. Cl. .......................... 422/57; 422/100; 422/58; 436/180

(58) Field of Classification Search ............ 422/57, 422/100, 58; 436/180
See application file for complete search history.

(56) References Cited

U.S. PATENT DOCUMENTS

| | | | |
|---|---|---|---|
| 4,426,451 A * | 1/1984 | Columbus | 436/518 |
| 4,761,381 A * | 8/1988 | Blatt et al. | 436/165 |
| 4,876,067 A | 10/1989 | Deneke et al. | |
| 5,004,923 A * | 4/1991 | Hillman et al. | 250/341.3 |
| 5,039,617 A * | 8/1991 | McDonald et al. | 436/69 |
| 5,286,454 A * | 2/1994 | Nilsson et al. | 422/102 |
| 5,520,883 A | 5/1996 | Charlton et al. | |
| 5,611,999 A | 3/1997 | Dosmann et al. | |
| 5,681,484 A * | 10/1997 | Zanzucchi et al. | 506/40 |
| 5,700,695 A | 12/1997 | Yassingzadeh et al. | |
| 5,723,284 A | 3/1998 | Ye | |
| 5,814,522 A | 9/1998 | Zimmer et al. | |
| 6,300,138 B1 | 10/2001 | Gleason et al. | |
| 6,916,410 B2 | 7/2005 | Katsuki | |
| 2002/0009387 A1 | 1/2002 | Hirayama | |
| 2003/0007893 A1* | 1/2003 | Purcell | 422/58 |

FOREIGN PATENT DOCUMENTS

| | | |
|---|---|---|
| EP | 0 269 240 A1 | 6/1988 |
| EP | 0 443 231 A1 | 2/1990 |
| EP | 0 483 117 A2 | 4/1992 |
| EP | 0 974 840 A2 | 1/2000 |
| JP | 08145980 | 6/1996 |
| JP | 09133673 | 5/1997 |

OTHER PUBLICATIONS

In re Rose, 220 F.2d 459, 105 USPQ 237 (CCPA 1955).*

* cited by examiner

*Primary Examiner*—Jill Warden
*Assistant Examiner*—Lore Ramillano
(74) *Attorney, Agent, or Firm*—Nixon Peabody LLP

(57) ABSTRACT

A device that is intended for the sampling of fluids, comprises a base and a lid. Between the base and the lid there is provided an opening and a first open-sided channel extending from the opening to a second open-sided channel for the collection of fluid therein. The depth of the second channel is smaller than that of the first channel.

19 Claims, 3 Drawing Sheets

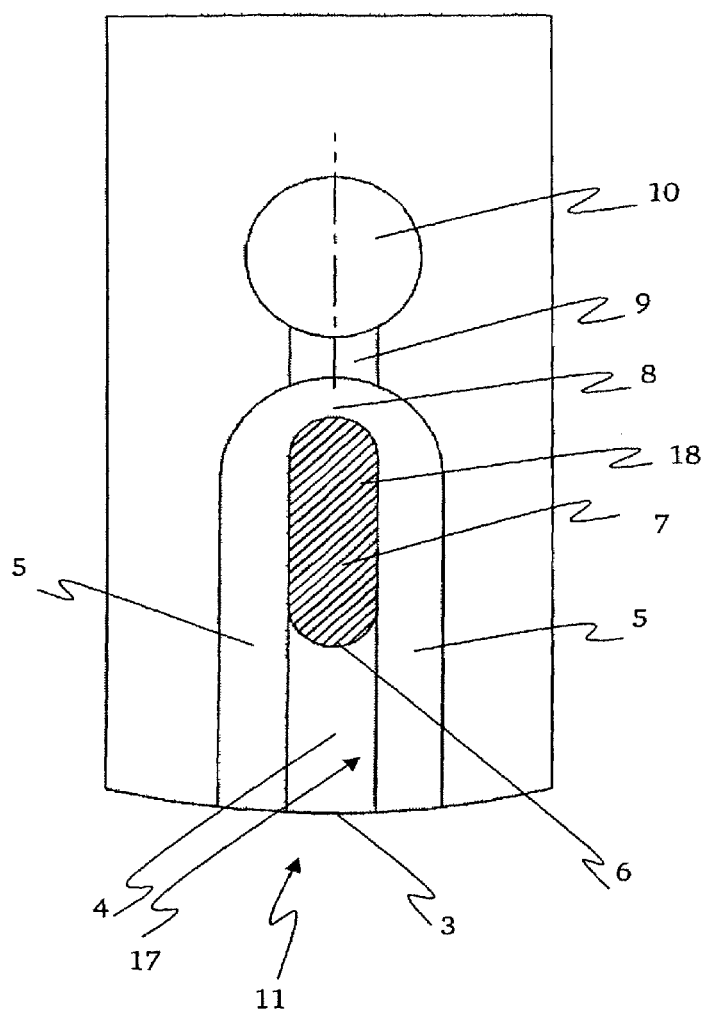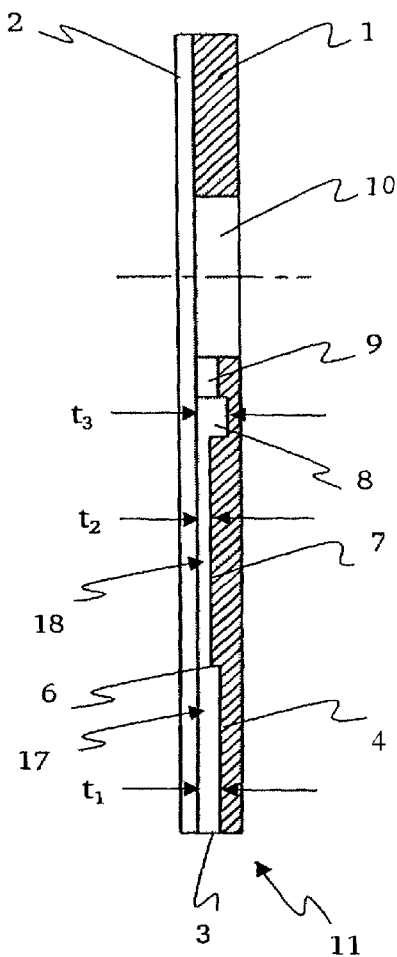
FIGURE 1
FIGURE 2

FLUID COLLECTING AND MONITORING DEVICE

The present invention relates generally to fluid collecting and monitoring devices and, more particularly, to a device for obtaining a sample of body fluid, such as blood.

There are a number of problems with the devices available in the prior art. One such piece of prior art is disclosed in Glenn Purcell's U.S. Application No. 60/303,550 entitled "Volume meter testing device". This document discloses a device for collecting and testing blood samples. One problem that is recognised in this document is that of air contaminating the sample and resulting in an inaccurate reading. The prior art device sets about solving this problem by forming a read area that is open sided, that is, one having no side walls. The test fluid arrives in the read area from a transfer area via a capillary gap that has no ceiling or floor and the transfer area itself is fully enclosed. This is a complex structure and requires a high level of dimensional accuracy in the various areas.

Test devices available in the prior art generally work by making a puncture wound in the skin, placing a vacuum device over the puncture, and applying the vacuum until a bead of blood is formed. The vacuum device is then removed and a test device is brought into contact with the bead to collect a sample.

A major disadvantage of this system is that the size of blood bead generated by the vacuum stage is variable. If the blood bead is too small then the test device will not collect enough blood and the vacuum has to be re-applied to draw extra blood from the skin. This is a problem for most amperometric devices, where it is important that the test volume is filled in one attempt. If the blood bead is too small and the test device is not completely filled, the test usually has to be repeated causing more pain and inconvenience to the user.

One of the aspects on which the prior art remains silent is the issue of blood left on the skin. The main aim of the prior art is in regard to picking up a sufficient quantity of blood to perform an accurate test and it is specifically stated that once the pick up area is full and there is sufficient blood in the device to perform an accurate reading, then the device can be removed from contact with the skin. However, if the blood drop has a volume greater than that required to perform the test then this blood will be left on the skin and the present invention aims to enable enough blood to be obtained to perform the test whilst leaving the skin clean by continuing take up of fluid beyond that strictly necessary to perform the test.

The choice of material from which the device of the present invention is made is influenced by the surface energies of the fluids under test. As the device operates by capillary action the fluid must have an internal contact angle between the bead of fluid and the surface of less than 90°. For this to occur the surface energy of the surface is more than, or similar to, the surface energy of the fluid. The surface energy is determined by the surface chemistry of the materials and also the surface roughness. The smaller the angle between the surface of a bead of fluid and the surface, the faster the fluid will move through the device.

The present invention aims to overcome the problems associated with the prior art and accordingly there is provided a device for sampling a fluid comprising: a base; a lid; and, between the base and the lid, an opening, a first open-sided channel extending from the opening to a second open-sided channel for the collection of fluid therein, the depth of the second channel being smaller than that of the first channel.

Preferably, the device further comprises a step between the first and second channels.

Vent channels may be provided that surround the first and second open-sided channels.

The open sides of the channels may be small in comparison to the width of the channels.

The device may further comprise a vent through which air can be removed from the vent channels. This vent may be situated beyond the second channel.

The volumetric space within the first channel is preferably 0.4-1.3 µl and the volumetric space within the second channel is preferably 0.4-1.0 µl.

The first and second channels may be aligned to form a substantially straight passageway.

The lid and base may be bonded together to contain the channels.

Preferably, a surface of the second channel is coated with a reagent.

The lid of the device may be translucent or transparent such that a colour change in the reagent may be analysed externally.

The device may further comprise a pair of electrodes disposed within the second channel to enable measurement of a change in current flowing between the electrodes.

There is also provided a method of collecting a fluid sample using a device according to the present invention, wherein the method comprises: placing the device adjacent to a fluid drop and allowing capillary action to collect the fluid into the device.

The fluid collected in the first channel may be transferred to the second channel by capillary action.

Alternatively the fluid may continue to be collected by the first channel after the transfer to the second channel has commenced.

The fluid may be collected from multiple beads of fluid from different surfaces.

The method may further comprise placing the device adjacent to a fluid drop such that the lid is closer to the drop than the base and allowing capillary action to collect the fluid into the device. The present invention has a number of advantages over the prior art. Firstly the simplicity of the structure with two open sided capillary channels surrounded by vent channels allows a very high efficiency of fluid transfer between the two capillary channels. This simplicity also has the advantage that the device is comparatively simple to manufacture and construct. The device can be manufactured in two parts: a base and a lid. Each of these may be injection moulded, cast or thermoformed or processed in sheet form and then stamped out. It is therefore easy to assemble the device by joining these two parts together. The movement of the fluid into the device takes place by capillary action encouraged by the provision of side and rear vent channels that allow air to be displaced from the device. This results in a high efficiency of collection from a surface.

The vent channels render the device robust to the effects of air inclusions and the relative lengths of the capillary and vent channels compared to their widths minimises the evaporation from the device. This means that the lid only has to span the comparatively small combined width of the vent and capillary channels. This has two advantages. Firstly, it is easier to get a tighter tolerance of the heights of the capillary gaps because the smaller span reduces the extent to which the centre can sag and reduce the gap thickness. Secondly, the lid can be made thinner and the device can then be inverted in use so that the lid is in contact with the collection surface where a much smaller bead of blood can bridge the thickness of the lid and be drawn into the capillary structure. This results in a high collection efficiency and also minimised waste. Furthermore, it minimises the amount of fluid left on the front of the device and thereby reduces the risk of contamination. The device has a minimum contact area with the skin resulting in very efficient collection and therefore very little fluid will be left on the surface. The device is able to collect a very small volume of fluid very accurately.

A number of devices according to the present invention may be formed side-by-side to form a frangible strip. If this is the case then one device may then be removed from the strip whenever it is needed. Alternatively, the devices may be manufactured in the form of a frangible strip but they may subsequently be separated for discrete packaging before they are distributed to the end user.

Examples of devices according to the present invention will now be described with reference to the drawings, in which:

FIG. 1 is a planar section of the device;

FIG. 2 is a schematic longitudinal sectional view through the device;

Figure 3:
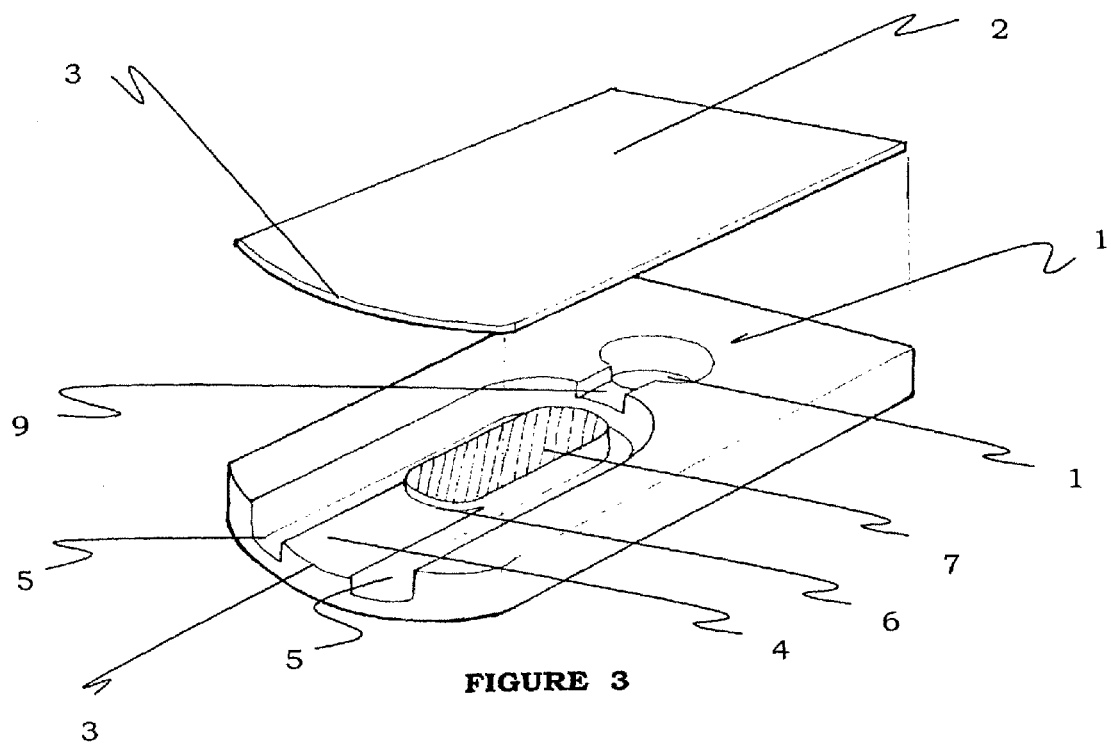
FIG. 3 is an exploded isometric view of the device.

The device 11 shown in the figures is a blood sampling device and has a base 1 and a lid 2 bonded to the base to form internal volumes which are used to collect and transfer small volumes of blood as described below.

The device 11 has a fluid collection point 3 at one end provided by the open end of a first channel 17 of depth (capillary gap) $t_1$ defined, between the base 1 and the underside of the lid 2, by a collection island 4 and the lid 2, and a second channel 18 of depth $t_2$ defined by a read island 7 and the underside of the lid 2. Side channels 5 and a rear channel 8 surround the islands 4, 7. The side channels 5 and rear channels have a greater depth (larger capillary gap) $t_3$ and the side channels are located one on each side of the islands 4 and 7. The device 11 also has a vent passage 9 communicating with the rear channels and a pin hole vent 10 communicating with the vent passage 9 to provide for venting of air from any of the channels 5, 8, 17 and 18.

In one embodiment, the base 1 and the lid 2 are manufactured from transparent materials and a reagent on the read island 7 is arranged to cause a colour change that can be analysed by an external photo-metric unit in use.

The fluid collection point 3 of the device 11 is placed in contact with the skin 12, typically within 0.5 mm of the puncture site 15. The device 11 is used in an inverted position such that the lid 2 is closer to the skin 12 than the base 1. The lid 2 is thinner in section than the base 1 so that the bead of blood only needs to grow enough in height to bridge the thickness of the lid 2 and the gap $t_1$ (see FIG. 2) at the fluid collection point 3. This minimises the volume of blood that is left on the skin 12 after the device has been removed.

Figure 4:
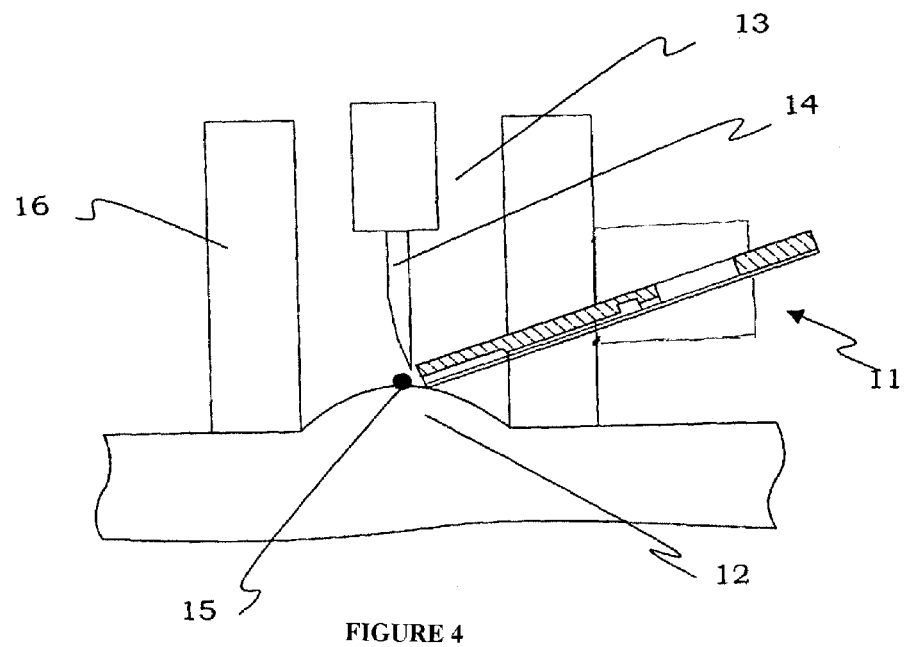
FIG. 4 is a partially sectioned side view of the device shown in use in the collection of a blood sample.

The device can be used to collect blood from the surface of skin as shown in FIG. 4 by means of a needle 14 which produces a small puncture 15 in the skin 12. A bead of blood is caused to flow from the puncture wound 15, for example by the application of an area of reduced pressure in the volume of air 13 directly above the skin 12, the volume of air 13 above the skin being defined by an appropriate structure 16. The absolute pressure in this area may be 0.1 to 0.7 bars and preferably 0.3 to 0.5 bars. An advantage of the present invention is that the read island 7 and collection island 4 can be stationary throughout the blood collection process. The device needs to be enclosed in the vacuum to prevent air leaking via the vent hole 10. The first channel 17 is kept in a known position relative to the puncture site. This means that the internal volume of the device can be smaller and the side channel can also be smaller and therefore the bead of blood required is smaller. This means, in turn, that the puncture in the skin required to extract sufficient blood to fill the device will be smaller and less painful.

The device 11 is held by the user at an angle relative to the surface of the skin 12 at the puncture site 15. The angle (typically between 30 degrees and 60 degrees) ensures that the contact area between the lid 2 and the skin 12 is minimised, which also reduces the volume of blood left on the surface of the test device and the skin when the test has been completed and the device 11 has been removed.

In use, the blood bead grows to bridge the gap $t_1$ between the lid 2 and the collection island 4 as mentioned above. Blood fills the channel 17 above the collection island 4 by capillary action until the fluid front of the blood contacts a step 6 at the front edge of the read island 7. The shape of the blood volume in the channel 17 above the collection island 4 is defined by the edge of the collection island 4 as there are no side walls. Once the blood volume has reached the step 6, the blood is in communication with the channel 18 (which has a gap $t_2$ above the read island 7). The majority of the volume of blood on the collection island 4 is then transferred onto the read island 7 by capillary action. Blood will not flow into the side channels 5 or the rear channel 8 because the gap $t_3$ between the base 1 and lid 2 at the side channels 5 and the rear channel 8 is significantly larger than the gaps $t_1$ and $t_2$ above the collection island 4 and the read island 7, respectively. Once the blood is transferred to the read island 7 the blood is exposed to a reagent previously coated onto either the area of the lid 2 opposite the read island 7 or onto the surface of the read island 7. The reagent reacts with an analyte in the blood to produce either a colour change or an electrical current (as described below).

Although The area of the read island 7 is slightly larger than the area of the collection island 4 the channel 17 associated with the collection island is deeper and therefore the overall volume of the collection island 4 is greater than that of the read island 7. This ensures that the read island 7 is completely filled when the blood transfers between islands. By having the collection volume larger than the read volume an incomplete fill of the read area is eliminated. The majority of the volume of the blood on the collection island 4 is transferred since the blood is only in contact (and pinned) at the two edges at the front of the collection island 4 and the lid 2 at the fluid collection point 3. The amount of blood left in the collection island 4 is the difference in volume between the collection 4 and read 7 islands. The difference in the size of the gaps $t_1$ and $t_2$ at the step 6 is sufficient to unpin the blood from these edges. The high efficiency transfer of blood between the islands means that the device is very efficient. Typically, the transfer efficiency between the collection island 4 and the read island 7 may be between 75% and 100%. The small volume of waste in the collection and transfer mechanisms also means that the initial volume of blood in the blood bead on the surface of the skin 12 can be very small. In a preferred example, the volume of blood on the skin collected and transferred to fill the read island 7 can be between 0.5 µl and 1.5 µl.

One advantage of the step 6 and the relative heights of the two channels 17, 18 is that the collection of blood will continue as blood moves by capillary action from the first channel 17 to the second channel 18 leaving the first channel 17 available to collect more blood from the surface of the skin 12. The transfer of the blood volume between the collection island 4 and the read island 7 can, however, occur rapidly if the surface energies of the islands and the lid as well as the sizes of the gaps $t_1$ and $t_2$ are controlled. This feature is an advantage if the method of analysing the analyte in the blood on the read island 7 is time-dependant. Blood will preferentially be picked up by the smaller capillary gap $t_1$ on the collection island 4 at, or near, the fluid collection point 3.

If the bead of blood is large enough, the device 11 can be used to collect an initially larger bead of blood, such that the larger initial volume and size of the blood bead blocks both side channels 5 and the collection island 4. In this case, the device will still operate since the air above the collection island 4 and the read island 7 can be displaced out of the device 11 through the vent 9 and the pin hole vent 10.

The widths of the side channels and collection islands are minimised as far as practicable so that the lid 2 can be made to be as thin as possible without compromising the assembly tolerances of the gaps $t_1$ and $t_3$. The thickness of the lid 2 is made as low as possible in order to minimise the size of the blood bead that can be collected from the surface of the skin. Another advantage of reducing the width of the collection island 4 is to control the position of the fluid front of the blood more accurately as it flows to the step 6. There is also an advantage to maximising the length of both islands 4, 7 as this maximises the length of the air diffusion path between the blood volume and the air outside the device 11. This minimises the effects of evaporation which in turn may affect the concentration of the analyte within the blood sample.

When the blood volume in the collection island 4 is transferred to the read island 7, the collection island is nearly emptied of blood. This has two potential advantages. Firstly, if blood continues to flow from the puncture site 15, the device will continue to collect blood onto the collection island 4 i.e. 'mopping' up excess blood from the skin 12. Secondly, if the device 11 is removed from the surface of the skin at the moment of blood transfer to the collection island 4 (this movement may be triggered by the appearance of blood on the read island 7), then there will be little or no blood left on the collection island 4 and the blood sample will be isolated inside the device 11 on the read island 7. This may reduce the risks of blood contamination.

Figure 5:
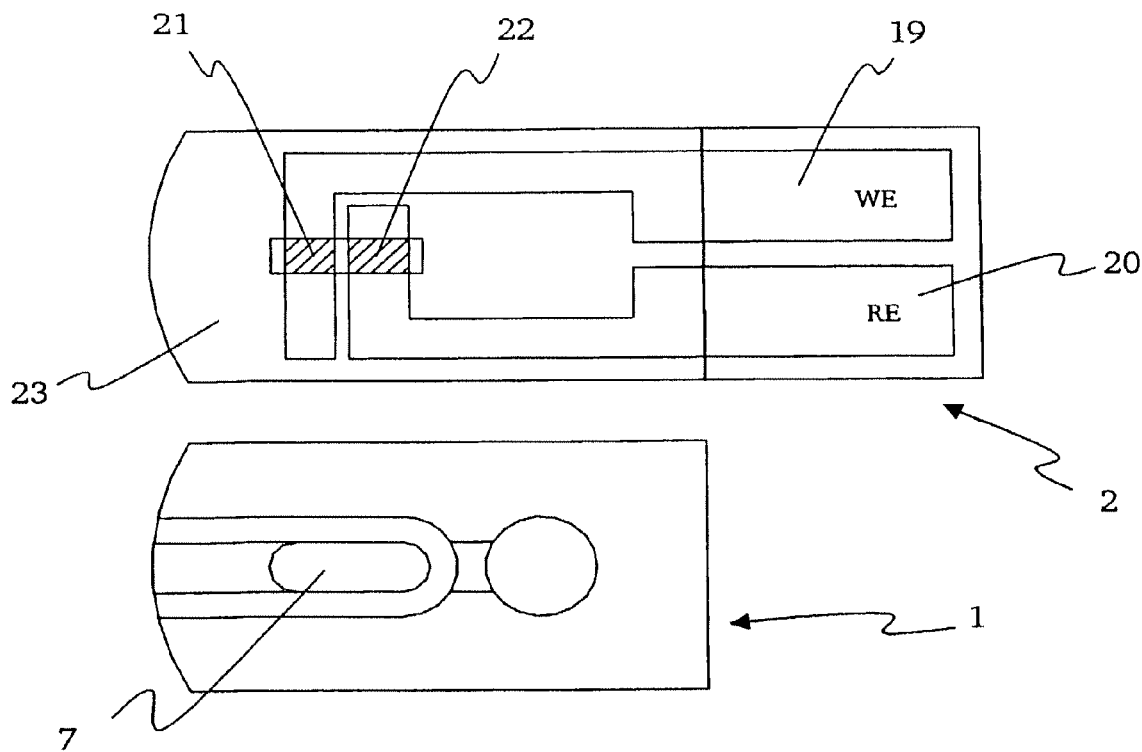
FIG. 5 is a plan view of the facing surfaces of a base and lid which includes electrodes.
Figure 6:
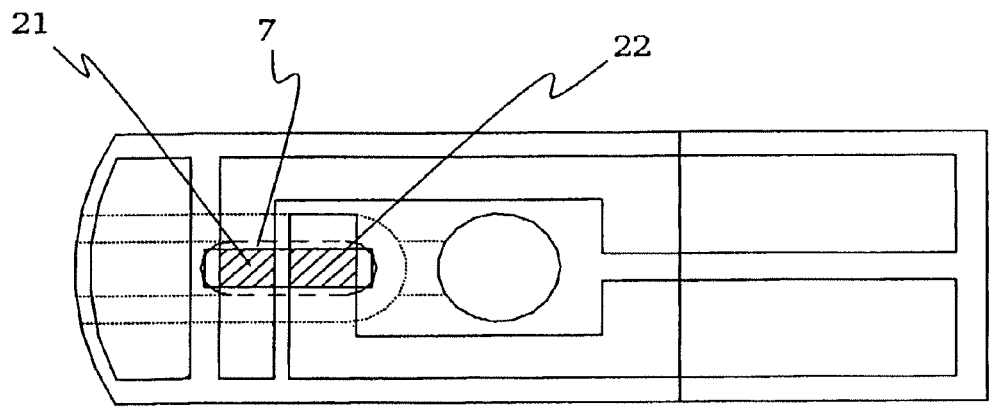
FIG. 6 is a plan view of the device of FIG. 5, after assembly, showing hidden detail.
Figure 7:
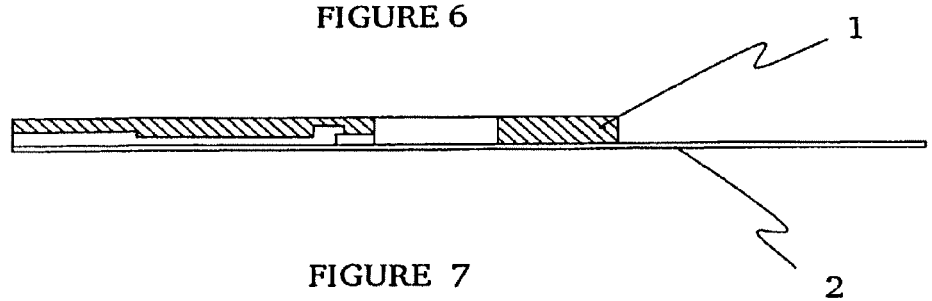
FIG. 7 is a longitudinal section through the device of FIG. 6.

In an alternative embodiment, illustrated in FIGS. 5, 6 and 7, two electrodes are formed onto the underside of the lid 2: a working electrode 19 and a reference electrode 20. Both electrodes are then coated with an insulating layer 23 over the area which will contact the base 1, and two small windows are left in the insulating layer to provide a working electrode window 21 and a reference electrode window 22 on the lid 2 opposite the read island 7. A chemical reagent is coated on to the read island 7.

When blood is transferred from the collection island 4 to the read island 7, the reagent dissolves in the blood and a reaction takes place that creates a small current which is related to the amount of glucose in the blood. The current creates a potential difference between the reference electrode 20 and the working electrode 19. The location and exposed area of the electrode windows 21 and 22 is very important. The area of the read island 7 and hence the volume of the initial blood sample can be reduced by minimising the exposed area of the electrodes 21 and 22 and also by their positional accuracy.

The invention claimed is:

1. A device for sampling a fluid comprising:
   a base;
   a lid;
   a fluid-collection point for initially receiving the fluid, the fluid-collection point being positioned between the base and the lid;
   a first open-sided channel for the collection of fluid therein, the first open-sided channel extending from the fluid-collection point;
   a second open-sided channel extending from the first open-sided channel, the depth of the second open-sided channel being smaller than the depth of the first open-sided channel; and
   at least one vent channel positioned adjacent to the first and second open-sided channels, the depth of the at least one vent channel being greater than the depth of the first open-sided channel.

2. The device according to claim 1, further comprising a step between the first and second open-sided channels.

3. The device according to claim 1, further comprising a vent through which air can be removed from the first and the second open-sided channels.

4. The device according to claim 3, wherein the vent is situated beyond the second open-sided channel.

5. The device according to claim 1, wherein the volumetric space within the first open-sided channel is 0.4-1.3 µl and the volumetric space within the second open-sided channel is 0.4-1.0 µl.

6. The device according to claim 1, wherein the first and second open-sided channels are aligned to form a substantially straight passageway.

7. The device according to claim 1, wherein the lid and base are bonded together to contain the first and second open-sided channels.

8. The device according to claim 1, wherein a surface of the second open-sided channel is coated with a reagent.

9. The device according to claim 8, wherein the lid of the device is translucent or transparent such that a color change in the reagent may be analyzed externally.

10. The device according to claim 8, further comprising a pair of electrodes disposed within the second open-sided channel to assist in measuring a change of current flowing between the pair of the electrodes.

11. A method of collecting a fluid sample, the method comprising the acts of:
   providing a device comprising
      a base,
      a lid,
      a fluid-collection point for initially receiving the fluid, the fluid-collection point being positioned between the base and the lid,
      a first open-sided channel for the collection of fluid therein, the first open-sided channel extending from the fluid-collection point,
      a second open-sided channel extending from the first open-sided channel, the depth of the second open-sided channel being smaller than the depth of the first open-sided channel, and
      at least one vent channel positioned adjacent to the first and second open-sided channels, the depth of the at least one vent channel being greater than the depth of the first open-sided channel; and
   placing the device adjacent to a fluid drop and allowing capillary action to collect the fluid into the device.

12. The method according to claim 11, wherein the fluid collected in the first open-sided channel is transferred to the second open-sided channel by capillary action.

13. The method according to claim 11, wherein fluid continues to be collected by the first open-sided channel after the transfer to the second open-sided channel has commenced.

14. The method according to claim 11, wherein the fluid is collected from multiple beads of fluids from different surfaces.

15. The method according to claim 11, wherein the device further comprises a step between the first and second open-sided channels.

16. The method according to claim 11, wherein the device further comprises a vent through which air can be removed from the first and the second open-sided channels.

17. The method according to claim 11, wherein the first and second open-sided channels are aligned to form a substantially straight passageway.

18. The method according to claim 11, wherein a surface of the second open-sided channel is coated with a reagent.

19. The method according to claim 11, wherein the device further comprises a pair of electrodes disposed within the second open-sided channel to assist in measuring a change of current flowing between the pair of the electrodes.

* * * * *

UNITED STATES PATENT AND TRADEMARK OFFICE
CERTIFICATE OF CORRECTION

PATENT NO.      : 7,604,775 B2
APPLICATION NO. : 10/216597
DATED           : October 20, 2009
INVENTOR(S)     : Pollock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1354 days.

Signed and Sealed this

Fifth Day of October, 2010

David J. Kappos
*Director of the United States Patent and Trademark Office*